United States Patent [19]

Baba et al.

[11] Patent Number: 5,112,872
[45] Date of Patent: May 12, 1992

[54] ANTISPASMODIC AGENT

[75] Inventors: Tatsuya Baba, Kawanishi; Norio Ogata, Osaka, both of Japan

[73] Assignee: Taiko Pharmaceutical Co., Ltd., Osaka, Japan

[21] Appl. No.: 448,468

[22] Filed: Dec. 11, 1989

[30] Foreign Application Priority Data

Jun. 1, 1989 [JP] Japan .................................. 1-140820
Sep. 21, 1989 [JP] Japan .................................. 1-247781

[51] Int. Cl.⁵ .............................................. A61K 31/05
[52] U.S. Cl. .................................................... 514/731
[58] Field of Search ...................... 514/731; 424/195.1

[56] References Cited

U.S. PATENT DOCUMENTS 4,608,258  8/1986  Yamanaka ...................... 424/195.1

OTHER PUBLICATIONS

A. N. Györy, Drugs, vol. 20, 1980, pp. 309-318 (1980).
R. V. Heatley et al., Gutt, vol. 23, 1982, pp. 1044-1047 (1982).
The Merck Index No. 7138, 9th ed., p. 954, 1976.

Primary Examiner—John W. Rollins
Attorney, Agent, or Firm—Armstrong & Kubovcik

[57] ABSTRACT

Disclosed are an antispasmodic agent comprising creosote or its component phenol derivative as an active ingredient, and the use of creosote or its component phenol derivative for treating spasms in a patient.

8 Claims, No Drawings

ANTISPASMODIC AGENT

BACKGROUND OF THE INVENTION

1. Technical Field

The present invention relates to an antispasmodic drug and more particularly to an antispasmodic composition containing creosote or one or more of its component phenol derivatives as an active ingredient.

2. Prior Technology

Creosote has heretofore been used as an intestinal antiseptic, an antidiarrheal drug indicated for intestinal antisepsis or an expectorant.

As such, creosote has been listed as an antiseptic in Section 1 of Antidiarrheal Drugs (Column V) in Standards of Approval to Manufacture Gastrointestinal Drugs on page 240 of the Guideline for Manufacture of Drugs, 1988 Edition (edited by Japan Official Compendium Association). It is also described in Hiroshi Ito: Yakurigaku (Pharmacology; Keiko-Do, 6th ed., published Jan. 5, 1983, page 416) that creosote is not only used as an intestinal antiseptic but exhibits expectorant activity when administered by inhalation. Furthermore, Hisashi Hano & Yoshio Aizawa: (Hirokawa Shoten, 3rd ed., published Oct. 15, 1974, page 216) mention creosote as an intestinal antiseptic. The Japanese Pharmacopoeia (JP) also states that creosote is not only used as an expectorant but is indicated in abnormal intestinal fermentation and food poisoning. The United States Dispensatory, 27th ed. (1973), also mentions on page 355 that creosote is used externally as an antiseptic and internally as an expectorant.

Thus, creosote has been used as an intestinal antiseptic or a drug for treating diarrhea based on intestinal antisepsis, or as an expectorant.

DISCLOSURE OF INVENTION

The inventor of the present invention conducted a series of intensive studies for finding pharmacological actions of creosote other than those associated with its usage as an antiseptic or an expectorant and discovered that surprisingly creosote and phenol derivatives contained in creosote had antispasmodic activity that was quite unexpected from the conventional knowledge, and that accordingly they inhibit the motility of smooth muscle such as that of the intestinal tract. The present invention has been accomplished on the basis of the above findings.

The present invention is, therefore, directed to an antispasmodic composition containing creosote or a phenol derivative, which is a component of creosote, as an active ingredient in combination with a pharmaceutically acceptable vehicle.

By virtue of the antispasmodic activity of creosote or its component phenol derivatives, the pharmaceutical composition of the present invention suppresses the motility of various smooth muscles in humans and animals. As such, the composition should be useful for the treatment of various symptoms requiring control of the motility or hypermotility of smooth muscle for relief, for example the relief of spasms of the gastric pylorus or the intestine, tonic biliary dyskinesia, and the pain associated with choledocholithiasis, cholecystolithiasis or urolithiasis, and the treatment of hypertension and angina pectoris. Furthermore, the composition should be useful for reducing the muscle tone as a pretreatment in endoscopy of the organs for facilitating insertion of the endoscope or for relaxing the gastrointestinal tract prior to radiography to assist in the passage of barium meal and thereby to facilitate the relief examination of the gastric wall or the like. In addition, because it inhibits the movement of the intestinal smooth muscle, the composition of the invention is useful for the treatment of diarrhea and other symptoms associated with hypermotility of the intestinal tract.

Predicated on the above-mentioned utility, the present invention also provides a method for treating spasms in patients requiring such treatment which comprises administering an antispasmodically effective amount of creosote or its component phenol derivative or derivatives to the patient.

Creosote, which is used as an active ingredient in accordance with the invention, is a known substance as listed in Japanese Pharmacopoeia XI, United States National Formulary XII and other official compendia. Creosote thus referred to is "wood creosote" obtained by distilling wood tar derived from trees such as beech, oak, maple, pine and other trees, particularly broad-leaved trees, subjecting the distillate further to fractional distillation and recovering the fraction in the boiling range of about 200° C.–230° C. (760 mmHg). This creosote is distinctly different from creosote derived from coal tar. Creosote used as the active ingredient of the pharmaceutical composition of the invention is a mixture comprising about 20 to 35 percent of guaiacol, about 15 to 25 percent of creosol, and various phenol derivatives such as phenol, cresols, xylenols, etc. It is available as a colorless or yellowish liquid having a characteristic smoky odor, an caustic, burning taste, and a specific gravity of not less than about 1.064. The inventor of the present invention has found that the respective component phenol derivatives contained in creosote also have antispasmodic activity similar to that of creosote. More specifically, each of guaiacol, creosol, phenol, xylenol, cresol, etc., occurring in creosote also has antispasmodic activity comparable to that of creosote. Therefore, in the present invention, the above-mentioned creosote can be used as it is or the phenol derivatives contained in the creosote may be used individually or in combination.

In accordance with the present invention, creosote or any of its component phenol derivatives can be used in the known pharmaceutical formulations. Thus, various pharmaceutical compositions can be prepared using ordinary pharmaceutically acceptable excipients and/or diluents in the conventional manner. These pharmaceutical compositions may be supplied in various dosage forms suited to the intended therapeutic applications, such as those suited to oral administrations, as typically represented by tablets, pills, powders, capsules, granules, liquids for internal use, etc. or those suited to intravenous, intramuscular, subcutaneous or intradermal administration, represented by injections, or further those dosage forms suited to rectal administration, typically suppositories.

For the manufacture of tablets, granules or powders, the hitherto-known carriers can be liberally selected and used. Such carriers include, among others, various excipients such as lactose, sucrose, glucose, starch, crystalline cellulose, etc., binders such as hydroxypropylcellulose, methylcellulose, gelatin, tragacanth, gum arabic, sodium alginate, etc., disintegrating agents such as starch, carboxymethylcellulose, calcium carbonate, etc., and lubricating agents such as magnesium stearate, talc, stearic acid and so on. If necessary, the tablets may be coated in the known manner to provide sugar-coated tablets, film-coated tablets, etc. or may be made available as two-layer tablets or multi-layer tablets. The granules and powders may also be clad in the known manner.

For the preparation of pills, various known carriers used commonly in the art can be employed. For example, various excipients such as powdered glycyrrhiza, glucose, wheat flour, etc., binders such as glycerin, water, syrup, gum arabic, tragacanth, gelatin, etc., and disintegrating agents such as medicinal yeast, arrowroot, laminaria flour, etc. can be employed.

For the preparation of capsules, various known carriers used commonly in the art can be employed. Thus, for example, various excipients such as lactose, olive oil, soybean oil, etc. can be used.

The liquids for internal use may be aqueous or oily suspensions, solutions, syrups or other preparations. For the preparation of such liquid preparations, conventional additives including various suspending agents such as sorbitol syrup, methylcellulose, gelatin, carboxymethylcellulose, etc. and emulsifying agents such as lecitin, sorbitan monooleate, gum arabic, etc. can be employed.

The injections may be any parenteral products such as injectable suspensions, solutions or emulsions in oily or aqueous vehicles and may contain suspending agents, stabilizers, dispersants and/or other formulating agents.

For the preparation of suppositories, various known bases used commonly in the art can be liberally selected and used. For example, cacao butter, glycerogelatin, macrogols, etc. can be employed. In the preparation of suppositories, emulsifiers and suspending agents may be used as required. Furthermore, such other additives as colors, corrigents, etc. may also be incorporated in the pharmaceutical compositions of the invention.

While the amount of creosote or its component phenol derivative or derivatives to be used in the pharmaceutical composition of the invention is not so critical and may be appropriately selected, it generally ranges from about 0.2 to 60 weight percent based on the weight of the total composition.

The dosage of the pharmaceutical composition of the invention is suitably determined depending on the patient's sex, age and body weight, the severity of the condition and the like. Generally, for administration by the oral or rectal route, the daily dose for an adult human is about 1 to 500 mg/kg body weight, preferably about 2 to 100 mg/kg body weight, and more preferably about 2 to 25 mg/kg body weight, each calculated as the active ingredient, i.e., creosote or its component phenol derivative(s). For parenteral administration by injection, the daily dose calculated as the active ingredient, i.e., creosote or its component phenol derivative(s) is generally about 0.2 to 300 mg/kg body weight, preferably about 0.2 to 50 mg/kg body weight, and more preferably about 0.5 to 5 mg/kg body weight for an adult human. The pharmaceutical composition of the present invention may be administered in about 2 to 4 divided doses daily.

EXAMPLES

Preparation examples and results of pharmacological tests are shown below.

| Preparation Example 1 Pills | |
|---|---|
| Ingredient | Amount (mg) |
| Creosote | 50 |
| Glycyrrhiza | 25 |
| Glycerin | 10 |
| Water | 50 |

The above ingredients in the indicated proportions were kneaded together and the resulting pill mass was mechanically divided and rounded to provide pills each containing 50 mg of creosote.

| Preparation Example 2 Capsules | |
|---|---|
| Ingredient | Amount (mg) |
| Creosote | 100 |
| Starch | 250 |

Creosote and starch were blended to provide a powdery mixture, which was filled into hard gelatin capsules to provide hard capsules each containing 100 mg of creosote.

| Preparation Example 3 Capsules | |
|---|---|
| Ingredient | Amount (mg) |
| Creosote | 100 |
| Olive oil | 200 |

Creosote was dissolved in olive oil and the solution was filled into soft gelatin capsules to provide soft capsules each containing 100 mg of creosote.

| Preparation Example 4 Tablets | |
|---|---|
| Ingredient | Amount (mg) |
| Creosote | 150 |
| Lactose | 250 |
| Methylcellulose | 3 |
| Magnesium stearate | 2 |
| Carboxymethylcellulose | 10 |

The above ingredients other than magnesium stearate were blended to provide the above formulation and the mixture was kneaded with water to give granules. After drying, the granules were mixed with magnesium stearate and compression molded. Alternatively, the above ingredients were mixed together and directly fed to a compression molding machine. Each of the above procedures gave tablets each weighing 415 mg.

| Preparation Example 5 Injection | |
|---|---|
| Ingredient | Amount (mg) |
| Creosote | 50 |
| Distilled water for injection | 2 ml |

The creosote in the indicated amount of 50 mg was dissolved in the distilled water for injection and the solution was sealed and sterilized to provide an injection.

| Preparation Example 6 Pills | |
|---|---|
| Ingredient | Amount (mg) |
| Guaiacol | 50 |
| Glycyrrhiza | 25 |

-continued

| Preparation Example 6 Pills | |
|---|---|
| Ingredient | Amount (mg) |
| Glycerin | 10 |
| Water | 50 |

The above ingredients in the indicated proportions were kneaded together and the resulting pill mass was mechanically divided and rounded to provide pills each containing 50 mg of guaiacol.

| Preparation Example 7 Capsules | |
|---|---|
| Ingredient | Amount (mg) |
| Guaiacol | 50 |
| Cresol | 50 |
| Olive oil | 100 |

Guaiacol and cresol were dissolved in olive oil and the solution was filled into soft gelatin capsules to provide soft capsules each containing 50 mg of guaiacol and 50 mg of cresol.

| Preparation Example 8 Tablets | |
|---|---|
| Ingredient | Amount (mg) |
| Creosol | 150 |
| Lactose | 250 |
| Methylcellulose | 3 |
| Magnesium stearate | 2 |
| Carboxymethylcellulose | 10 |

The above ingredients other than magnesium stearate were blended to provide the above formulation and the mixture was kneaded with water to make granules. After drying, the granules were mixed with magnesium stearate and compression molded. Alternatively, the above ingredients were mixed together and directly compression molded. Each of the above procedures gave tablets each weighing 415 mg.

Pharmacological Test 1

(a) Female Hartley guinea pigs weighing 400 to 600 g were fasted for 24 hours and, then, anesthetized by an intramuscular injection of 30 mg/kg of sodium pentobarbital. The abdomen was opened by midline incision and 5 cm strips of the intestine were excised: the ileum (5 cm) was excised from the ileocecum, excluding the most distal 15-cm portion, the jejunum (5 cm) was excised from the duodenojejunal junction, excluding a 15-cm portion from the duodenojejunal junction, the ileojejunal junction (5 cm) was excised from the distal part of the jejunum, and the colon (5 cm) was excised from the distal part, excluding a 15-cm portion from the anus. The intestinal strips were washed with Tyrode solution to remove the intestinal contents and each of them was suspended at a tension of 0.6-gw in a Mugnus chamber (KN-207, Natsume, Tokyo, Japan). The chamber was filled with 50 ml of Tyrode solution saturated with bubbled air and maintained at 37° C. Spontaneous contractions of the intestinal strips were recorded on a kymograph (Kymographion KN-215, Natsume) by means of an isotonic writing lever.

After 60 minutes of equilibration, creosote was cumulatively added to the Magnus chamber at 5-minute intervals and the contractile response of the intestinal strip was recorded each time. The degree of contraction of the strip was evaluated by measuring the average height of dominant peaks in a series of experiments and the percent inhibition of the contraction was calculated with the average peak height at the 0 g/ml level of creosote being taken as 100%. From the dose-response curve thus constructed, the dose of creosote that gives 50% inhibition, i.e. $IC_{50}$, was determined.

The results for the respective portions of the intestinal tract are shown in Table 1(a).

TABLE 1 (a)

| Portion of the intestinal tract | $IC_{50}$ (g/ml) |
|---|---|
| Ileum | $1.7 \times 10^{-5}$ |
| Ileojejunal junction | $1.5 \times 10^{-5}$ |
| Jejunum | $1.7 \times 10^{-5}$ |
| Colon | $1.3 \times 10^{-5}$ |

(b) Experiments on the inhibition of peristaltic motility of intestinal strips were carried out in the same manner as Experiment (a) except that guaiacol, creosol, cresol, phenol and xylenol, all of which are components of creosote, were respectively used in lieu of creosote.

Using strips of the ileum, the dose of each test compound causing 100% inhibition of the motility of the strip, i.e., $IC_{100}$, was assayed. The results are shown in Table 1(b).

Table 1(b) sets forth the corresponding result for creosote as well.

TABLE 1 (b)

| Test compound | $IC_{100}$ (g/ml) |
|---|---|
| Guaiacol | $1 \times 10^{-4}$ |
| Creosol | $1 \times 10^{-4}$ |
| Cresol | $1 \times 10^{-4}$ |
| Phenol | $1 \times 10^{-4}$ |
| Xylenol | $1 \times 10^{-4}$ |
| Creosote | $1 \times 10^{-4}$ |

It is apparent from Table 1(b) that creosote and its component phenol derivatives have antispasmodic activity, particularly an action to inhibit the motility of the intestinal tract.

Pharmacological Test 2

In this test, the inhibitory effect of creosote on the contractions of intestinal strips induced by agonists, namely acetylcholine and bradykinin, was investigated using the same apparatus as used in Pharamacological Test 1.

Strips of guinea pig ileum prepared in the same manner as in Pharmacological Test 1 were respectively suspended in 50 ml of Tyrode solution and allowed to equilibrate for 60 minutes. Then, acetylcholine was added to the Tyrode solution at a final concentration of $5 \times 10^{-9}$ g/ml and the degree of contraction (peak height) of the ileum strip was measured (control).

Then, the same ileum strip was washed and creosote was added to Tyrode solution at a final concentration of $2 \times 10^{-6}$ g/ml. After 3-min preincubation of the ileum strip, acetylcholine was added at a final concentration of $5 \times 10^{-9}$ g/ml. The contraction (peak height) was then measured.

Then, the ileum strip was washed and creosote was added to Tyrode solution at a final concentration of $4 \times 10^{-6}$ g/ml. After 3-min preincubation of the ileum strip, acetylcholine was added at a final concentration of $5 \times 10^{-9}$ g/ml. The contraction (peak height) is then measured.

Thereafter, following the same procedure as above, the peak height of contractions was similarly recorded after addition of creosote at levels of $8 \times 10^{-6}$ g/ml, $1.6 \times 10^{-5}$ g/ml, and so on.

The percentage of the peak height at each level of creosote relative to the control peak height (100%) was calculated and a creosote concentration-relaxation curve was constructed. From this curve, the concentration of creosote reducing the contractions induced by the agonist by 50%, namely $IC_{50}$, was determined.

$IC_{50}$ was also determined using bradykinin in the same manner as above except that the final concentration of bradykinin was $2 \times 10^{-8}$ g/ml.

The results are shown below in Table 2.

TABLE 2

| Agonist | $IC_{50}$ (g/ml) |
|---|---|
| Acetylcholine ($5 \times 10^{-9}$ g/ml) | $3.0 \times 10^{-5}$ |
| Bradykinin ($2 \times 10^{-8}$ g/ml) | $5.8 \times 10^{-6}$ |

It is apparent from Table 2 that creosote has antispasmodic activity.

Pharmacological Test 3

Female Wistar rats weighting 170 to 190 g were used. One week before the test, the rats were transferred for preliminary feeding to an air-conditioned laboratory room controlled at 20°-24° C. 40-70% R.H., a ventilation frequency of 12/hr and a 12-hr light and 12-hr dark cycle.

The individuals in poor general condition were culled out. The rats thus acclimatized for one week were divided into groups of substantially uniform mean body weight. Each group consisted of 10 animals. The rats were fasted for 18 hours beginning the day before treatment and saline solutions containing varying concentrations of creosote were orally administered in a uniform volume of 1 ml. Then, after an interval of 1 hour, 1 ml of castor oil was administered to each rat.

The animals were than observed for the onset of diarrhea following the administration of castor oil.

It is known that castor oil has the property to increase the motility of the intestinal tract and that rats given castor oil show diarrhea as a definitely observable symptom.

Thus, in the control group not premedicated with creosote, 98% of the rats had diarrhea within 2 hours after administration of castor oil. In the rats given creosote beforehand, the castor oil-induced enhancement of intestinal motility was suppressed dose-dependently and consequently the onset of diarrhea was inhibited.

The effective dose of creosote causing anti-diarrhea effect in 50% of rats within hour n after administration of castor oil, i.e., $ED_{50}$ (mg/kg) was determined. It was postulated that the antidiarrheal effect was positive when neither soft stool nor watery stool was observed. The results are shown in Table 3.

TABLE 3

| n (hours) | $ED_{50}$ (mg/kg) |
|---|---|
| 1 | 53 |
| 2 | 150 |
| 3 | 165 |
| 4 | 175 |
| 5 | 213 |
| 6 | 225 |
| 7 | 280 |

It is apparent from Table 3 that with increasing dosage, creosote inhibited the enhancement of intestinal motility for increasing time.

Actue toxicity

Regarding the acute toxicity of creosote and its component phenol derivatives which are active ingredients of the pharmaceutical composition according to the present invention, the oral $LC_{50}$ values in rats are shown in Table 4.

TABLE 4

| Active ingredient | $LD_{50}$ (mg/kg) |
|---|---|
| Creosote | 885 |
| Phenol | 530 |
| Guaiacol | 725 |
| o-Cresol | 1350 |
| m-Cresol | 2020 |
| p-Cresol | 1800 |

What is claimed is:

1. A method of treating spasm in a patient in need of such treatment which comprises administering an antispasmodically effective amount of creosote or one or more of its component phenols to said patient.
2. A method as defined in claim 1 wherein said component phenols are selected from the group consisting of guaiacol, creosol, phenol, xylenol and cresol.
3. A method as defined in claim 1 which comprises administering creosote or one or more of its component phenols by oral or rectal route in a dosage of about 1 to 500 mg/kg body weight/day.
4. A method as defined in claim 1 which comprises administering creosote or one or more of its component phenols by oral or rectal route in a dosage of about 2 to 100 mg/kg body weight/day.
5. A method as defined in claim 1 which comprises administering creosote or one or more of its component phenols by oral or rectal route in a dosage of about 2 to 25 mg/kg body weight/day.
6. A method as defined in claim 1 which comprises administering creosote or one or more of its component phenols by injection in a dosage of about 0.2 to 300 mg/kg body weight/day.
7. A method as defined in claim 1 which comprises administering creosote or one or more of its component phenols by injection in a dosage of about 0.2 to 50 mg/kg body weight/day.
8. A method as defined in claim 1 which comprises administering creosote or one or more of its component phenols by injection in a dosage of about 0.5 to 5 mg/kg body weight/day.

* * * * *